US011389640B2

(12) United States Patent
Morozov et al.

(10) Patent No.: US 11,389,640 B2
(45) Date of Patent: Jul. 19, 2022

(54) DEVICES AND METHODS FOR DETERMINING HEART FUNCTION OF A LIVING SUBJECT

(71) Applicants: HIGHDIM GMBH, Riehen (CH); Universitätsspital Basel, Basel (CH)

(72) Inventors: Oleksii Morozov, Riehen (CH); Patrick Hunziker, Basel (CH)

(73) Assignees: HighDim GmbH, Riehen (CH); Universitätsspital Basel, Basel (CH)

(*) Notice: Subject to any disclaimer, the term of this patent is extended or adjusted under 35 U.S.C. 154(b) by 256 days.

(21) Appl. No.: 16/479,438

(22) PCT Filed: Jan. 19, 2018

(86) PCT No.: PCT/EP2018/051255
§ 371 (c)(1),
(2) Date: Jul. 19, 2019

(87) PCT Pub. No.: WO2018/134330
PCT Pub. Date: Jul. 26, 2018

(65) Prior Publication Data
US 2019/0381226 A1 Dec. 19, 2019

(30) Foreign Application Priority Data

Jan. 19, 2017 (EP) ..................... 17152103

(51) Int. Cl.
*A61M 60/50* (2021.01)
*A61B 5/00* (2006.01)
(Continued)

(52) U.S. Cl.
CPC ........... *A61M 60/50* (2021.01); *A61B 5/0031* (2013.01); *A61B 5/01* (2013.01); *A61B 5/029* (2013.01);
(Continued)

(58) Field of Classification Search
CPC .. A61M 60/50; A61M 60/135; A61M 60/871; A61M 2205/3317;
(Continued)

(56) References Cited

U.S. PATENT DOCUMENTS 6,112,598 A 9/2000 Tenerz et al.
6,976,965 B2 12/2005 Corl et al.
(Continued)

FOREIGN PATENT DOCUMENTS

EP 1839551 A1 3/2007
EP 2662113 A2 11/2013
(Continued)

OTHER PUBLICATIONS

International Search Report and Written Opinion issued in International Application No. PCT/EP2018/051255 dated Aug. 1, 2018.

*Primary Examiner* — Rex R Holmes
(74) *Attorney, Agent, or Firm* — Hoffmann & Baron, LLP

(57) ABSTRACT

The present invention relates to systems, methods and algorithms for determination of heart pump function and their use in livings subject are described.
The invention further relates to complementary parts of such systems that work best in combination.
Medical catheters, sheaths and shafts are disclosed that carry an arrangement of integrated digital sensor systems-on-chip (SoC) in the portion thereof residing inside the body. These devices combine at their portion that resides inside the body, the complete chain of signal transduction, signal analog-to-digital conversion and digital signal transmission, and allow to acquire single and multiple physical entities in a single setup. In specific instances the devices integrate wireless data transfer functionality, and in specific instances they integrate wireless energy harvesting for battery-free functionality.

(Continued)

The present invention further describes complementary monitor systems that are suited for reception, processing and analysis of data acquired by such catheters/sheaths/shafts to yield a robust assessment of cardiac performance.

Moreover, the present invention relates to innovations which render such systems applicable to patients with and without cardiac assist devices.

14 Claims, 2 Drawing Sheets

(51) Int. Cl.
| | |
|---|---|
| *A61B 5/01* | (2006.01) |
| *A61B 5/0205* | (2006.01) |
| *A61B 5/029* | (2006.01) |
| *A61B 5/05* | (2021.01) |
| *A61B 8/06* | (2006.01) |
| *A61M 60/135* | (2021.01) |
| *A61M 60/871* | (2021.01) |
| *A61B 5/0215* | (2006.01) |

(52) U.S. Cl.
CPC ........... *A61B 5/02055* (2013.01); *A61B 5/05* (2013.01); *A61B 5/7264* (2013.01); *A61B 5/742* (2013.01); *A61B 8/065* (2013.01); *A61M 60/135* (2021.01); *A61M 60/871* (2021.01); *A61B 5/02154* (2013.01); *A61B 5/02158* (2013.01); *A61B 2562/0233* (2013.01); *A61B 2562/0247* (2013.01); *A61B 2562/0271* (2013.01); *A61M 2205/3317* (2013.01); *A61M 2205/3334* (2013.01); *A61M 2205/3344* (2013.01); *A61M 2205/3365* (2013.01); *A61M 2205/3523* (2013.01); *A61M 2205/8206* (2013.01); *A61M 2230/50* (2013.01)

(58) Field of Classification Search
CPC .. A61M 2205/3334; A61M 2205/3344; A61M 2205/3365; A61M 2205/3523; A61M 2205/8206; A61M 2230/50; A61B 5/0031; A61B 5/01; A61B 5/02055; A61B 5/029; A61B 5/05; A61B 5/7264; A61B 5/742; A61B 8/065; A61B 5/02154; A61B 5/02158; A61B 2562/0233; A61B 2562/0247; A61B 2562/0271; A61B 2560/0214; A61B 2560/0219; A61B 2560/04; A61B 2560/0462; A61B 5/6852; A61B 5/0215; A61B 5/027; A61B 5/0002; A61B 5/6876

See application file for complete search history.

(56) References Cited

U.S. PATENT DOCUMENTS

| | | | |
|---|---|---|---|
| 9,345,436 | B2 | 5/2016 | Hunziker et al. |
| 2009/0216292 | A1 | 8/2009 | Pless et al. |
| 2011/0301414 | A1* | 12/2011 | Hotto ................ A61B 1/00055 600/114 |
| 2014/0194753 | A1 | 7/2014 | Dekker et al. |
| 2015/0289929 | A1* | 10/2015 | Toth .................... A61B 5/6858 600/372 |
| 2017/0238950 | A1* | 8/2017 | Yang ..................... A61L 29/02 |

FOREIGN PATENT DOCUMENTS

| | | | |
|---|---|---|---|
| WO | WO 2011/062683 | A1 | 5/2011 |
| WO | WO 2016/044651 | A1 | 3/2016 |

* cited by examiner

DEVICES AND METHODS FOR DETERMINING HEART FUNCTION OF A LIVING SUBJECT

CROSS-REFERENCE TO RELATED APPLICATIONS

This application is the U.S. National Phase of, and Applicant claims priority from, International Application No. PCT/EP2018/051255, filed on 19 Jan. 2018, and European Patent Application No. 17152103.2, filed on 19 Jan. 2017, both of which are incorporated herein by reference in their entirety.

BACKGROUND

Pump action of the heart is a fundamental vital function of the body and its accurate determination is important in many disease states, in sports and in other application fields. The determination of cardiac output, defined as the integrated forward flow of blood from the left ventricle over a time interval, correlates in a very nonlinear fashion with various measurable biological parameters. This correlation is further influenced by the presence and activity of artificial devices, e.g. heart assist pumps, in various locations of the circulatory system. There are a number of clinical measurement techniques of heart pump function, including cardiac catheterization, thermodilution and pulse waveform analysis, but all methods have specific limitations, including inaccuracy, ineffectiveness, invasiveness, and practical difficulties in their clinical application.

Need for New Catheters

Determining and monitoring of the performance of the heart, in particular cardiac output, often relies on assessment of a single, key physiologic parameter that is taken as surrogate for the—inaccessible—cardiac output parameter of interest.

Typically, measurement of parameters for computing cardiac output (CO) rely on invasive catheters. Such catheters often contain either a fluid line that propagates the pressure inside the body to a sensor outside the body, or it consists of optical line that propagates a light signal from a measurement location inside the body to a sensor outside the body, or it contains an electric line that transports an analog signal from inside the body e.g. from a thermistor, to an analog-to-digital converter outside the body. The transmission of physical or analog signals from inside the body to a transducer outside the body is susceptible to mechanical or electrical noise; such catheters are often difficult and expensive to manufacture; their handling in clinical practice is laborious; the multiple connections (analog wires, fluids) and the external power supply and signal transfer lines that are needed for functionality render patient management more complex.

Future systems for cardiac output determination should therefore innovate in catheter designs to overcome these limitations.

Using a single parameter for determination of cardiac output, as is typically done with thermodilution or pulse contour analysis, has several disadvantages:

1) the surrogate parameter may not accurately represent the required but inaccessible heart function parameter;

2) surrogate values may be confounded by other physiologic and technical parameters;

3) the reliance on a single sensor renders the method sensitive to sensor errors including noise, drift, sensor inaccuracy, sensor displacement; and 4) cardiac assist systems, be they implanted, external, or based on percutaneous catheters, are typically major confounders of currently used algorithms for computing cardiac output (CO).

Need for Multiple Parameters and Their Integrated Analysis

In contrast, heart function determination methods that are based on combination of multiple biological signals have the potential to overcome weaknesses mentioned, in part by delivering more robust primary signals and by allowing control of confounding factors. One important practical limitation of current clinical practice when monitoring multiple vital parameters is that this leads to increased complexity of patient management, because each additional sensor typically comes with its own cable for power supply and sensor signal output, thereby increasing complexity and cost.

Thus, future systems for cardiac output determination should preferably have the capability of a) acquiring multiple signal modalities, with a minimum amount of equipment, in synchronous fashion, b) analysing such multiple signal parameters in combination, and c) being applicable and reliable in patients that receive mechanical circulatory support.

This implies the need for innovation in cardiac monitor devices and algorithms to be used in conjunction with catheters/sheaths/shafts in this invention.

PRIOR ART

Most current state-of-the art monitoring catheters are capable of probing a single physical modality inside the body, that in typical scenarios is guided to the outside of the body where an external transducer converts the physical signal to an analog signal and the analog signal is converted in an additional stage to a digital signal, the typical example being current invasive pressure monitor catheters.

In addition, there exist medical pressure wires that can be placed in the body to measure a single signal that transduce pressure at the wire tip by converting it to an analog signal inside the body, and guide the analog signal to a catheter portion outside the body, with the device needing to be connected to a second device (the interface box) outside the body for analog to digital signal conversion and data transmission (Radi Patent 1997, see http://patents.justia.com/patents/6112598), (Volcano patent 2002, see http://patents.justia.com/patent/6976965). There exist medical Doppler wires that allow to extract a single ultrasound Doppler signal from the body, by reading out not only low frequency pressure but also high frequency pressure oscillation through a similar catheter; also in this case, an analog signal is guided from the catheter tip to a location outside the body where additional equipment is required for analog to digital conversion (Volcano patent 2002, see http://patents.justia.com/patent/6976965). In addition, a limited number of multimodal sensing catheters for medicine exists, that typically have an analog sensing element and a number of channels of fibers that guide a physical signal (pressure, light) out of the body to be transduced to an electrical signal outside the body. An example is the CCOmbo/SvO2 pulmonary artery catheter from Edwards Life Science. It combines an analog temperature sensing thermistor at its tip inside the body, contains fluid filled lumina that allow pressure determination outside the body by an added external pressure transducers, and optical fibers that guide an optical spectrum to outside the body, whereby the actual optical sensors transduce the physical signal into a stream of digital information are located outside the body.

Prior Art in Monitors for Computing Cardiac Output

The main methods employed currently are the pulmonary artery catheter and in the PiCCO system and the pulmonary form the main body of prior art.

a) Pulmonary Artery Catheter in Detail: Pulmonary artery catheters were long considered the mainstay of cardiac output monitoring in clinical practice, although it is well known that they are not accurate in various circumstances. The simplest pulmonary artery catheters measure a temperature curve in the pulmonary artery after injection of cold fluid into the right atrium. They are often difficult to place, have a risk of infection and of pulmonary artery damage, and a large measurement variability, in particular when tricuspid (heart) valve insufficiency is present, like in most severely sick individuals. The alternative Fick method for cardiac output determination relies on the oxygen content in blood drawn from the pulmonary artery drawn by the pulmonary artery catheter, and in the arterial circulation. As this method relies on the knowledge of total body oxygen consumption (which is typically altered in sick individuals), it is unreliable. Yet another method is continuous monitoring of central venous oxygen saturation by optical fiber-equipped catheters. Because this parameters depends on many confounders unrelated to cardiac output, it is not considered as good surrogate of cardiac output. All these mentioned pulmonary artery catheter based methods are old with multiple expired patents covering them.

b) PiCCO system in detail: The PiCCO system relies on bolus thermodilution measurement in a central artery after injection of a cold fluid bolus injected into a central vein, thus needing two separate, central vascular catheters. Technically, it consists of a thermistor on a tip of a catheter with an external signal digitizer and data transmission in a separate, external module. In addition, PiCCO can use the blood pressure contour guided out from a central artery through a fluid filled lumen to be monitored using an external pressure transducer followed by an external analog-to-digital converter and data transmission.

c) HighDim prior art (U.S. patent application Ser. No. 13/827,063) describes an apparatus and methods to compute cardiac output based on multiparameter physiologic data that are analyzed using multidimensional nonlinear optimization to compute cardiac output. A limitation of this method is that it does not account for the case when a circulation assist device, e.g., an implantable cardiac pump, contributes to the cardiac output of the individual. In such a case, the true cardiac output is underestimated because the machine contribution is not accounted for; in addition, the implantable cardiac pump will induce changes in the circulatory system that are unaccounted for in the algorithm learning process described in U.S. patent application Ser. No. 13/827,063.

Improvements in medical monitoring technology is desirable because they can lead to improved patient management.

Measuring multiple physical signals at a location inside the body has the potential to yield information that is suited as input to algorithms and systems that can exploit the complementary, redundant, and mutually dependent information content of signals, as described below.

Definition of Terms

By the expression "inside the body" any configuration is hereby encompassed wherein a medical invasive device is, in total or limitedly to just a body portion thereof, inserted into one of a blood vessel, a body cavity and a body tissue.

With Catheter, a hollow tube of a diameter less than a centimetre and more than hundred micrometer is meant that has a primary function to connect a body compartment, typically the intravascular compartment, with the outside of the body for with the goal of one of, infusion of therapeutic liquids, withdrawing blood, and measuring the hydrostatic pressure through a water column guided to the outside of the body.

With Sheath, a hollow tube of a diameter of less than a centimetre and more than 100 micrometers is meant that serves to contain in its main lumen an elongated inner object and guides it from the outside of the body to inside the body. Such a sheath may contain zero or more additional hollow lumina for other purposes, in addition to the object-carrying main lumen.

With Shaft, an elongated object with a diameter of less than a centimetre and more than 100 micrometers is meant that has the primary function to carry on its part inside the body a number of functional subsystems that includes at least one of, a pump, and a sensor array. C/S/S is here used for "catheters, sheaths, shafts".

Miniaturized digital sensor System-On-Chips (SoC) as described here combine, in integrated package having a diameter measured perpendicular to a device axis, not larger than the available space at target location inside the body, (typically smaller than 5 square millimeters for catheters and shafts arranged for diagnostic purposes only, and typically smaller than 20 square millimetres for sheaths that are used in conjunction with heart pumps), the necessary circuits to yield a digital encoding of a quantitative measurement of a physical modality, including at least the signal to analog transduction, analog-to-digital conversion, and digital transmission. The use of such miniaturized digital sensors has the following advantage: a) the transmission of analog signals, which is prone to noise and bias, is eliminated: b) the number of noise sources is reduced because of integrated transducing and digitizing sensor elements; c) digital multiplexing of the output of multiple sensors allows minimizing the number of signal lines; d) the manufacture of the (C/S/S) is simplified because fewer electrical connections are needed, and e) digital sensors with very low power requirements exist. The size limit of those sensors is important because clinically tolerable access size to blood vessels is limited and typically ranges up to from 0.5 to 3 millimeter device diameter for purely diagnostic use, up to 5 mm for shafts of circulation assist devices, and up to 8 mm for catheters used in extracorporeal circulation. Power requirements of sensors are important for clinical application and are preferably low, to simplify power supply and avoid excessive heating of the sensor that is clinically undesirable.

Computer

In connection with the invention the term "computer" can relate to any suitable computing system. In particular, the computer can be a desktop computer, a laptop computer, a tablet a smartphone or a similar device as well as an embedded computing system such as a microcontroller or any other single- or multi-processor embedded system.

Energy Harvesting

Energy harvesting is used to designate a process whereby a device extracts electrical energy from a physical energy source in its surroundings without having a wired connection to the energy source. Energy harvesting technology is well known to a practitioner in the field. In the context of this patent, the term coil designates an electrical coil.

Heart Pump

A heart pump is defined as a medical device that pumps blood from one compartment of the blood circulation to another compartment of the blood circulation. Typical pumps include: a) extracorporeal pumps that have a mechanical pump part outside the body; b) catheter-based pumps that have the mechanical pump part inside the body and are mounted on the tip of a shaft that crosses the skin; and c) fully implantable pumps that have the mechanical pump part inside the body and no part except a power supply cable that crosses the skin.

Deep Neural Network

In machine learning field, a deep neural network (DNN) is an artificial neural network (ANN) with multiple hidden layers of units between the input and output layers.

Deep Believe Network

In machine learning field, a deep believe network is a type of a deep neural network, comprising multiple layers of latent variables with connections between the layers but not between units within each layer.

SUMMARY

According to the present invention, the need for more precise measuring of signals which reflect the heart performance of a patient and allow the extraction of cardiac output parameters better representing the cardiac output is settled by a medical invasive device; a method of computing cardiac output and apparatus as it is defined by the features of the respective independent claims Preferred embodiments are subject of the dependent claims.

In particular, the present invention deals with an innovative configuration for medical invasive devices wherein, for instance, signal transduction, analog-to-digital signal conversion and digital signal transmission are moved into the portion of the catheter arranged to be located inside a vessel lumen, by using miniaturized digital sensor SoCs.

Accordingly, medical digital sensor SoC arrays are mounted on catheters, sheaths and shafts at their location inside the body.

The advantages deriving from such innovative configurations comprise 1) reducing or eliminating the need for signal transducer modules outside of the body, thus simplifying industrial production, distribution and clinical use, and 2) the elimination of hydrostatic columns for pressure propagation, of wires carrying sensitive analog signals and of optical lines for signal transmission. The proposed setup consists of devices in the shape of (C/S/S) that comprise miniaturized digital sensors at their tips performing the stages of physical signal sensing, signal transduction, analog-to-digital signal conversion and digital signal transmission, at a location positioned inside the body.

Moreover, a multitude of sensor SoCs that measure different, complementary physical signals, can be placed into a portion of a medical (C/S/S) arranged to be positioned inside the body, according to the present invention.

Sensors to be used in connection with the present invention are described below more in detail.

In line with the above innovative configuration, an arrangement of medical digital sensor SoC and SoC arrays is provided wherein the sensors are mounted at the portion of a medical invasive device that is located inside the body. Integrated multimodal sensor arrays for vital biosignal monitoring can be thus integrated in one of:
  a) the shaft of a circulatory assist device;
  b) a free standing shaft;
  c) a vascular access sheath; and
  d) a intravascular catheter.

A number of useful sensor combinations are possible and below given as non-limiting examples.

The integration has the advantage of reducing the number of access cables to a patient to one per sensor array and leads to improved practicability in a clinical scenario.

In addition to that, in the following devices are described in the shape of a medical (C/S/S) comprising an arrangement of digital sensor SoCs with digital transmission at a location arranged to be positioned inside the body, that incorporate a digital interface at their part arranged to be located outside the body to allow to connect a connector cable for power supply and digital data transfer.

While the embodiments conceived according to the above aspect of the invention already simplify and improve medical monitoring, it is still desirable to also give up wired power supply and communication. For these reasons, further improvements are desirable.

According to another aspect of the present invention, wireless transmitting catheters and/or sheaths and/or shafts can be designed with integrated Medical Sensor SoCs and SoC arrays. Accordingly, an integrated multimodal biomedical sensor array may be driven by an integrated battery and read out by wireless data transmission.

Accordingly, a further aspect of the present invention consists of a medical (C/S/S) with an arrangement of miniaturized digital sensor SoCs at their portion arranged to be located inside the body in combination with a wireless communication chip and a miniaturized battery located at the portion arranged to be located outside the body in a single embodiment. This allows to eliminate the need for cables for power supply and communication and may greatly improve clinical practicability. It will also improve electrical safety because no metallic connection to the patient is needed.

According to a further possible embodiment of the present invention, a medical (C/S/S) can be designed with an arrangement of miniaturized digital sensors arranged to be located inside the body and a connector in combination with a pluggable module that comprises a small battery and electronics for wireless signal transmission.

This has the advantage that an empty battery can be replaced by plugging in a charged replacement module.

From the large spectrum of potential sensor modalities that can be used as elements for the sensor array according to the present invention, the following are preferred:

miniaturized digital pressure sensor SoCs are beneficial, because they allow to measure the blood pressure (an important parameter of cardiac function) at given locations but in contrast to conventional sensors neither require the fluid-filled pressurized access channels nor the extracorporeal transducers that are typically used in conventional pressure monitoring catheters, and do not rely on analog signal transmission along the device. A preferred example of a miniaturized digital temperature sensors are beneficial because they allow to monitor body temperature and also because they allow to measure temperature fluctuations that occur after injection of boli of cool fluids; the character and timing of such temperature fluctuation after such thermal bolus injection are related to cardiac performance.

miniaturized digital light emitters and receivers for multiple wavelengths allow determining the spectral components of the blood and thus derive blood oxygenation using standard formulas; it is well known that blood oxygenation and its time course contains relevant information about cardiopulmonary function.

miniaturized digital vibration sensors allow sensing the dynamic, turbulent aspects of blood flow and may thereby contribute information to cardiac function.

ultrasonic Doppler sensors allow to measure blood flow velocity and thereby contribute information cardiac function.

direct ultrasonic flow sensors allow to determine wave velocity between two points and thereby to measure blood flow velocity directly, contributing information about cardiac function.

voltage sensor: allows direct detection of electrical heart action timing and frequency; allows measurement of local body impedance.

While the above ameliorations over the prior art improve patient management, the elimination of the need for a battery is still desirable because it has the potential to simplify manufacture, to improve shelf life, to reduce cost, and to reduce the risk of battery leakage. Further innovations are therefore desirable.

In a further aspect of the present invention, a device in the shape of a medical (C/S/S) comprising an arrangement of digital sensor SoCs at their portion arranged to be located inside the body with a wireless transmission electronics in one of, their portion arranged to be located outside the body and a pluggable module, is additionally equipped with an energy transfer and harvesting mechanism that allows to eliminate the need for a power supply through battery or cable. A battery-free, energy harvesting medical sensor array, in combination with catheters, sheaths and carrying shafts, is described. Independence of batteries can lead to more compact designs and to improved practicability because battery discharge is not an issue anymore.

Recent progress in wireless technology has made it possible to produce wireless sensors, which can be battery driven, thus reducing the need for cables.

Recent progress in energy harvesting has made it possible to harvest energy from environmental sources, like electromagnetic fields, sunlight, vibration, heat, etc.

The following energy harvesting mechanisms can be used: a) inductive energy transmission through electromagnetic fields; b) capacitive energy transmission; c) solar-cell based energy transmission; d) vibration based energy harvesting and d) thermoelectric energy transduction. A preferred version is the inductive energy transmission because larger energies can typically be transferred compared to other setups, but high voltages on the energy transmitter side are not required.

Furthermore, the present invention deals with algorithms for combining vital signals with technical control signals and motor parameters. It discloses a novel combination where multiparameter biosignal monitoring as known in the state of the art is combined with technical control signals and performance signals originating from a catheter-based or implantable circulatory pump, thus going beyond the state of the art. This has the practical advantage of rendering the biosignal analysis applicable to patients who have a catheter-based or implanted circulatory assist device.

The present invention also deals with methods to be used in conjunction with multiparameter signals that are suited for patients with and without heart assist devices.

One method combines a number of physiologic data sources with a number of parameters derived from a heart assist device and builds a non-linear mathematical model that correlates those data to targeted cardiac output values. The physiologic data vectors include one or more measurable or derivable parameters such as: systolic and diastolic pressure, pulse pressure, beat-to-beat interval, mean arterial pressure, maximal slope of the pressure rise during systole, the area under systolic part of the pulse pressure wave, gender (male or female), age, height, weight, and diagnostic class. The parameters derived from a heart assist device include one or more of the following: device blood flow, device type, device performance setting, motor current, rotation frequency, pressure inside device, pressure across device. The target cardiac output values are acquired using various methods, across a plurality of individuals. Multidimensional nonlinear optimization is then used to find a mathematical model which transforms the source data to the target CO data. The model is then applied to an individual by acquiring physiologic data for the individual and applying the model to the collected data.

A step consists of adding heart assist device parameters in addition to the physiological parameters for building a model. In contrast to what was done in prior art, this invention uses the joint information of biology and assist device to achieve a more robust result. Using setups described in prior art, assist device acted as confounders, while in the current invention the machine parameters are now sources of useful information. Practically, this will expand the patient spectrum to which such monitoring can be applied.

In another embodiment, measurements of the same biological parameter (preferably blood pressure and its time course) is performed at two different locations in the same compartment of the circulation. The advantage of this approach is that pulse wave propagation, that is a highly nonlinear biologic process, goes into the mathematical model as additional information and has thereby the potential to render the mathematical model more robust. In contrast, neglecting the pulse wave propagation as done in usual clinical practice renders wave propagation of the pulse wave a confounding factor for cardiac output analyses.

The present invention furthermore discloses a monitor designed for allowing the above described determination of a cardiac performance based on combinations of medical signals and motor control/performance signals; as well as:

a system for monitoring vital signs based on combinations of C/S/S equipped with Medical Sensor SoC, optional wireless data transmission, optional wireless energy harvesting and a monitor that is suited for multimodal signals;

the use of a system combining biosignals and motor parameters for patient monitoring;

the use of wireless sensor array data transmission for patient monitoring;

the use of energy harvesting catheters, sheats, and shafts for patient monitoring; and the use of systems combining wireless medical sensor arrays for patient monitoring.

BRIEF DESCRIPTION OF THE DRAWINGS

The medical invasive device according to the present invention, employed in connection with the method of computing cardiac output of a living subject according to the present invention, is described in more detail herein below by way of exemplary embodiments and with reference to the attached drawings, in which.

DETAILED DESCRIPTION

Figure 1:
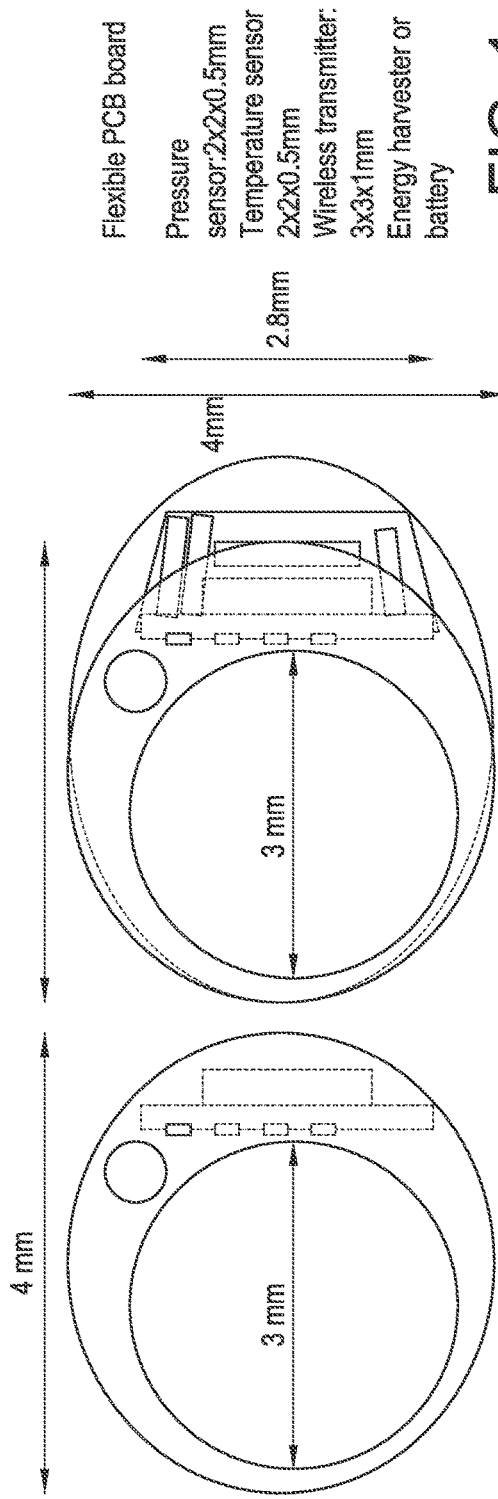
FIG. 1 is a cross-section of an embodiment of a medical invasive device according to the invention.
Figure 2:
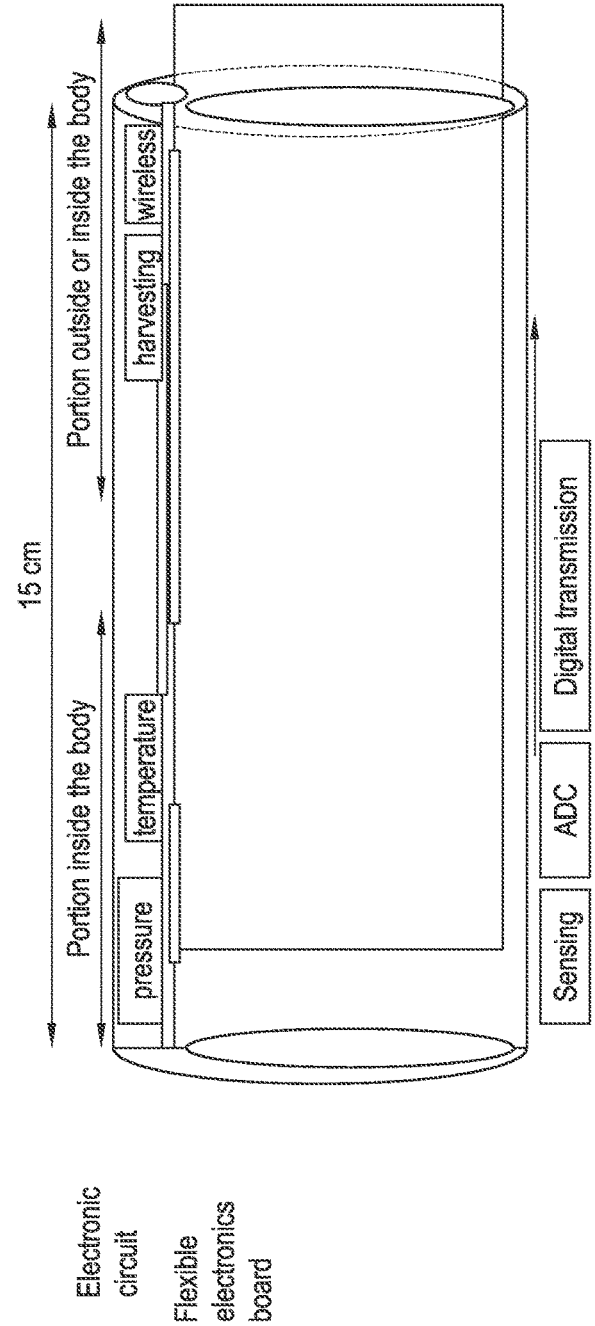
FIG. 2 is a side view of an embodiment of a medical invasive device according to the invention.
Figure 3:
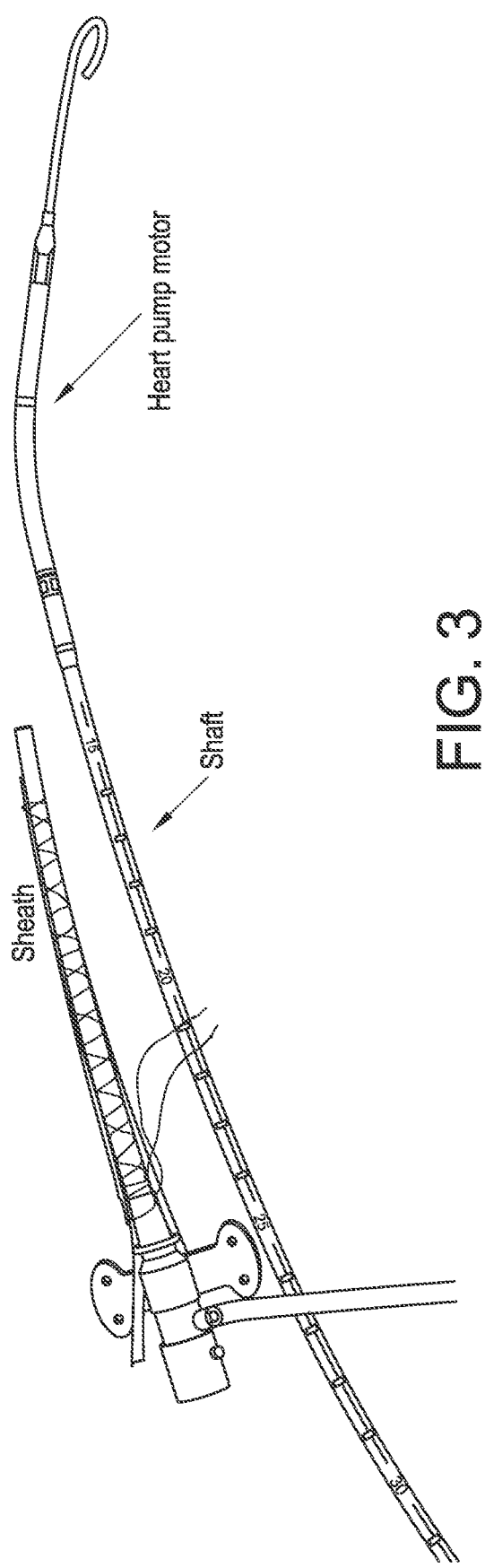
FIG. 3 represents an embodiment of a sheath with integrated flexible electronics board and receive coil circuit and an embodiment of a shaft with integrated emitter coil circuit according to the invention.
Figure 4:
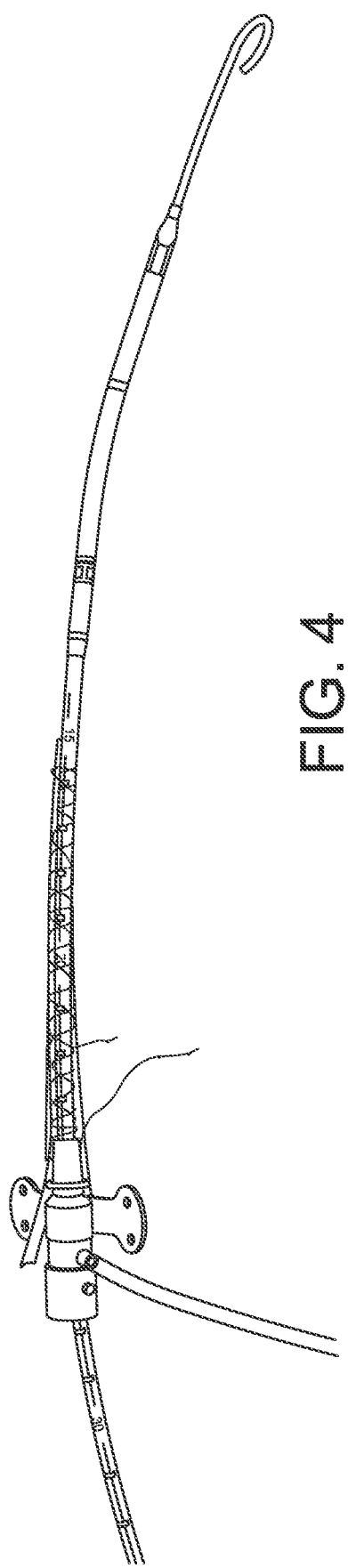
FIG. 4 is an embodiment of a sheath (outer element) covering a segment of a shaft (inner element) in a coaxial orientation according to the invention.

Sensor catheter: In one embodiment of a (C/S/S) according to the present invention, a standalone monitoring catheter was constructed by polymer casting, having 0.018" inner lumen (intended for a guide wire) and an outer diameter of 2.8 mm, smaller than the sheath of current pulmonary artery catheters. Contained in the polymer cast is a flexible electronics board from polymer with a diameter of 2.4 mm and a length of 15 mm that connects the portion of the device inside the body with the portion outside the body. At its portion inside the body, the flexible board carries two digital sensors in one miniaturized package, namely a digital pressure sensor and a digital temperature sensor, with integrated analog-to-digital conversion and a digital signal transmission, packed into a single plastic body of 2*2*0.76 millimeters (STMicroelectronics, part Nr. LPS22HB), and at the portion outside the body, the flexible electronics board carries a connector for wired readout.

Wireless sensor catheter: In one embodiment of a (C/S/S) according to the present invention, a standalone monitoring catheter was constructed by polymer casting, having 0.018" inner lumen (intended for a guide wire) and an outer diameter of 2.8 mm, smaller than the sheath of current pulmonary artery catheters. Contained in the polymer cast is a flexible electronics board from polymer with a diameter of 2.4 mm and a length of 15 mm that connects the portion of the device inside the body with the portion outside the body. At its portion inside the body, the flexible board carries two digital sensors in one miniaturized package, namely a digital pressure sensor and a digital temperature sensor, with integrated analog-to-digital conversion and a digital signal transmission, packed into a single plastic body of 2*2*0.76 millimeters (STMicroelectronics, part Nr. LPS22HB), and at the portion outside the body, the flexible electronics board carries miniaturized chips comprising digital communication and wireless transmission (TI) and a small battery (type).

For successful energy harvesting, the energy harvested over time must be sufficient to drive the sensors at the desired measurement intervals (typically ranging between 10 milliseconds to 4 hours) and to drive wireless transmission at its desired transmission intervals (typically ranging between 100 milliseconds to 4 hours).

For inductive, wireless powering of the device, an external electromagnetic field needs to be built up. The requirements for this electromagnetic field include safety, capability for sufficient energy transfer, and compatibility with existing regulation. We have identified several design variants:

1) a custom designed energy receiving coil on a C/S/S and a matched emitter coil with similar resonant frequency are constructed and optimized such that the received energy is sufficient to drive the electronics integrated in the C/S/S. An example of such a setup is shown in the examples. In a preferred setup, such a combination works in a radiofrequency band that legally permits medical use, and works with a distance from energy emitter to energy receiver that facilitates bedside application, e.g. at 30-50 cm from the catheter insertion site.

2) an emitting field is created by an emitter in vicinity to the patient bed. Such energy transmission is well known in the field and is, for example, described in detail in the ISO standard 15693 and performs energy transmission and data transmission up to 1-1.5 meters. An advantage of this solution is that clinically desirable distance from the patient is maintained that simplifies patient care; a disadvantage of this solution is that the energy transmitted is low and typically allows only very limited functionality of the electronics on the receiving device.

3) an emitting field is created by a transmitter put into proximity (up to 10 cm) of the exit site of the device in the skin. Transmission of energy and data is well known in the field and is described in detail in the ISO standard 14443. An advantage of small distance is that the energy yield at the receiver side is improved and thereby allows more functionality on the device side, and a disadvantage is that an emitter coil at this distance from the patient may hinder nursing care of a patient; also, this setup requires that the emitter coil remains in sufficient proximity over time.

4) an emitting field is created by a transmitter according to a standard for wireless charging, e.g. the Qi standard. The Qi standard is originally intended for high-current charging of devices like mobile phones in close proximity (centimeters) to the emitting coil, but we found that a modified setup can be used that allows a larger distance (up to 1 m) to transfer smaller amounts of energy. While the amount of energy transferred is much smaller (decaying approximately with the cube of the distance), this is still sufficient for the very low-power electronics used in our setup.

5) an emitting field is created by the catheter crossing a sensor-equipped sheath. This scenario is preferred when the sensor-equipped sheath is used to guide the shaft of a circulatory assist device into the body, thus assuring close proximity of emitting coil and sensor-equipped device and optimizing energy transfer. A working example of this setup is given below.

Other upcoming standards for wireless interaction with transmission of energy and information, e.g. the EPC standard, differ in frequency band, data transmission protocols and other details but can be used wherever specific requirements allow it.

In all options, higher frequencies typically facilitate the design of emitter and receive coils because the desired resonance frequencies can be achieved with lower inductances of coils and smaller capacitors.

Wireless energy transfer/harvesting: In a number of experiments, energy harvesting by coils integrated into our (C/S/S) was tested. To this end, a copper wire receive coil (200 micrometer copper wire, 25 windings, coil diameter 4 mm, coil length 85 mm, inductance estimated by resonant tuning 0.384 microhenry) was integrated into a sheath, cast in PDMS. A resonant circuit was produced by connecting a 1 nanofarad capacitor parallel to the receive coil. Resonance in the receive circuit was observed at the frequency of 8.12 MHz.

In addition, an energy transmit coil was built from 200 micrometer copper wire, 30 windings, coil diameter of 2 mm and coil length of 150 mm, having a measured inductance of 0.377 microhenry. The transmit coil was placed into the shaft of a catheter-based cardiac assist device. A resonant circuit was produced by connecting a capacitor of 1 nanofarad parallel to the emitter coil. Resonance in the emitter circuit was observed practically at the same resonance frequency (8.2 MHz) as in the receive circuit. The shaft was inserted into the sheath so that the emitter coil was positioned coaxially in respect to the receive coil. The emitter circuit connected in serial to a 100 Ohm current-limiting resistor was driven by a sinusoidal signal with frequency of 8.12 MHz and amplitude of 10 V generated by a waveform generator Hewlett Packard 33120A. The receive circuit was connected in serial to a diode TS4148 used for rectification. The rectified signal was fed to a voltage regulator built based on LM3671 step-down DC-DC converter from Texas Instruments.

Successful energy transfer from the emitter circuit to the receive circuit was documented as follows:

the voltage across a resistive load of 1 kOhm connected to the output of the voltage regulator was 3 V that corresponds to the current of 3 mA and the power of 9 mW. According to the specification of the pressure and temperature sensor LPS22HB and specification of Bluetooth Low Energy (LE) IC nrf52832 from Nordic Semiconductor this power is sufficient for acquisition of the pressure and temperature signals and transmission of the acquired data to a remote Bluetooth LE device.

These results confirm that sufficient energy can be transferred to the energy harvesting, sensor carrying catheter.

Wireless energy transfer/harvesting: In one embodiment of a (C/S/S) according to the present invention, a copper wire receiver coil (200 micrometer copper wire, 20 windings, coil diameter 5 mm, coil length 4 mm, inductance estimated by resonant tuning 1.57 microhenry) was integrated into a sheath, cast in PDMS. A resonant circuit was produced by connecting a 100 picofarad capacitor parallel to the receive coil. Resonance in the receive circuit was observed at the frequency of 12.76 MHz. The emitter coil was separate from the catheter and was implemented with 200 micrometer copper wire, 2 windings, 88 mm coil diameter and coil length 4 mm, having a measured inductance of 1.56 microhenry. A resonant circuit was produced by connecting a 100 picofarad capacitor parallel to the emitter coil. Resonance in the emitter circuit was observed at 12.75 MHz. The emitter circuit connected in serial to a 1 kOhm current-limiting resistor was driven by a sinusoidal signal with frequency of 12.76 MHz and amplitude of 10 V generated by a waveform generator Hewlett Packard 33120A. An SMD1206 red LED was connected in parallel to the receive circuit. Successful energy transfer from the emitter circuit to the receive circuit was documented as follows: when the emitter coil was positioned in proximity of the receive coil (at a distance of 1-3 mm) the LED started to shine indicating availability of at least several hundred of microwatts of harvested electrical power according to LED specification.

Wireless, energy harvesting sensor catheter: In one embodiment of a (C/S/S) according to the present invention, an access sheath for a catheter-based cardiac assist device was constructed by polymer casting, having an inner open lumen of 2.8 mm and an outer diameter of 4 mm, corresponding to the size requirements for access sheaths of the cardiac assist device. Contained in the polymer cast is a flexible electronics board from polymer with a diameter of 3 mm and a length of 15 mm that connects the portion of the device inside the body with the portion outside the body. At its portion inside the body, the flexible board carries two digital sensors in one miniaturized package, namely a digital pressure sensor and a digital temperature sensor, with integrated analog-to-digital conversion and a digital signal transmission, packed into a single plastic body of 2*2*0.76 millimeters (STMicroelectronics, part Nr. LPS22HB), and at the portion outside the body, the flexible electronics board carries miniaturized chips comprising digital communication, wireless transmission and energy harvesting (TI).

The present disclosure also comprises the following further embodiments:

Embodiment 1 is a medical invasive device having a body portion arranged to be inserted into one of, a blood vessel, a body cavity and a body tissue, that is equipped with an electronic circuit and that incorporates in the body portion a sensor arrangement and a digital data transmission arrangement.

Embodiment 2 is the medical invasive device of embodiment 1, having an analog-to-digital conversion arrangement in its body portion.

Embodiment 3 is the medical invasive device of the embodiment 1 or of the embodiment 2, wherein the medical invasive device has an outside portion arranged to be positioned outside the body.

Embodiment 4 is the medical invasive device of any one of the embodiments 1 to 3, whereby the electronic circuit comprises a sensor arrangement having a temperature sensor, a pressure sensor, a vibration sensor, an ultrasound sensor, a light sensor, a voltage sensor or any combination thereof.

Embodiment 5 is the medical invasive device of any one of the embodiments 1 to 4, whereby the sensor arrangement comprises at least two sensors for measurement of different physical signals.

Embodiment 6 is the medical invasive device of any one of the embodiments 1 to 5, whereby the sensor arrangement comprises at least three sensors for measurement of different physical signals.

Embodiment 7 is the medical invasive device of any one of the embodiments 1 to 6, wherein the medical invasive device has a shaft being an elongated object that carries the body portion and being arranged to traverse the skin level.

Embodiment 8 is the medical invasive device of any one of the embodiments 1 to 7, wherein the medical invasive device is a catheter that is an elongated object arranged to enter the body and comprises a number of fluid columns.

Embodiment 9 is the medical invasive device of any one of the embodiments 1 to 8, wherein the medical invasive device is a sheath that is an elongated object arranged to guide one of, a catheter, a shaft of a therapeutic device, and a shaft of a heart pump.

Embodiment 10 is the medical invasive device of any one of the embodiments 1 to 9, wherein the body portion has a transversal cross-sectional area of less than 60 square millimetres.

Embodiment 11 is the medical invasive device of any one of the embodiments 1 to 10, wherein the body portion has a transversal cross-sectional area of less than 20 square millimetres.

Embodiment 12 is the medical invasive device of any one of the embodiments 1 to 11, wherein the body portion has a transversal cross-sectional area of less than 5 square millimetres.

Embodiment 13 is the medical invasive device of any one of the embodiments 1 to 12, whereby the electronic circuit comprises a wireless data transmission unit.

Embodiment 14 is the medical invasive device of any one of the embodiments 3 to 13, whereby the outside portion comprises a wireless data transmission unit.

Embodiment 15 is the medical invasive device of embodiment 14, whereby the wireless data transmission unit is disconnectable from a base of the outside portion.

Embodiment 16 is the medical invasive device of any one of the embodiments 1 to 15, powered by one of, a battery and a capacitor.

Embodiment 17 is the medical invasive device of any one of the embodiments 3 to 16, wherein a battery or a capacitor are disconnectable from the outside portion.

Embodiment 18 is the medical invasive device of any one of the embodiments 1 to 17, whereby the electronic circuit comprises a harvesting unit arranged to harvest energy from energy sources that are not connected to the medical invasive device by wires.

Embodiment 19 is the medical invasive device of any one of the embodiments 3 to 18, whereby the outside portion carries a harvesting unit.

Embodiment 20 is the medical invasive device of embodiment 19, wherein the harvesting unit comprises a coil for harvesting electromagnetic energy.

Embodiment 21 is the medical invasive device of any one of the embodiments 19 or 20, wherein the harvesting unit comprises a solar cell.

Embodiment 22 is the medical invasive device of any one of the embodiments 18 to 21, wherein the harvesting unit comprises a vibration-based power generator.

Embodiment 23 is the medical invasive device of any one of the embodiments 18 to 22, wherein the harvesting unit comprises a thermoelectric generator.

Embodiment 24 is the medical invasive device of any one of the embodiments 1 to 23, comprising a harvesting unit with a receiving coil circuit that is tuned to a frequency such that an electromagnetic field typically produced in its proximity elicits an energy transfer to the coil that is sufficient to drive the electronic circuit on the body portion and optionally any other electronic circuits of the medical invasive device.

Embodiment 25 is the medical invasive device of any one of the embodiments 1 to 24, comprising a harvesting unit with a receiving coil circuit arranged for energy harvesting from an electromagnetic field, whereby the field is produced by a number of emitting coil circuits, and whereby an emitting coil circuit has a resonance frequency within 10% of the resonance frequency of the receive coil circuit, and preferably within 1% of the resonance frequency of the receive coil circuit, and particularly preferably within 0.1% of the resonance frequency of the receive coil circuit.

Embodiment 26 is the medical invasive device of any one of the embodiments 1 to 25, comprising a number of coil circuits arranged for energy harvesting from an electromagnetic field in the frequency band ranging from 5.725 to 5.875 GHz.

Embodiment 27 is the medical invasive device of any one of the embodiments 1 to 26, comprising a number of coil circuits arranged for energy harvesting from an electromagnetic field in the frequency band ranging from 2.4 to 2.5 GHz.

Embodiment 28 is the medical invasive device of any one of the embodiments 1 to 27, comprising a number of coil circuits arranged for energy harvesting from an electromagnetic field in the frequency band ranging from 902 to 928 MHz.

Embodiment 29 is the medical invasive device according to any one of the embodiments 1 to 28, comprising a number of coil circuits arranged for energy harvesting from an electromagnetic field in the frequency band ranging 13.553 to 13.567 MHz.

Embodiment 30 is the medical invasive device according to any one of the embodiments 1 to 29, comprising a number of coil circuits arranged for energy harvesting from an electromagnetic field in the frequency band ranging from 6.765 to 6.795 MHz.

Embodiment 31 is the medical invasive device according to any one of the embodiments 1 to 30, comprising a number of coil circuits arranged for energy harvesting from an electromagnetic field in the frequency band ranging from 235 to 275 kHz (Power Matters Alliance (PMA) defined band).

Embodiment 32 is the medical invasive device according to any one of the embodiments 1 to 31, comprising a number of coil circuits arranged for energy harvesting from an electromagnetic field in the frequency band ranging from 110 to 205 kHz (Wireless Power Consortium (WPC) defined band).

Embodiment 33 is a kit comprising an outer element that is a sheath according to one of the embodiments 9 to 32, and an inner element being a shaft or a catheter that comprises a coil circuit, whereby the outer element covers at least a segment of the inner element.

Embodiment 34 is a kit according to embodiment 33, whereby the inner element is arranged to be in a coaxial orientation relative to the outer element.

Embodiment 35 is a kit according to embodiment 33 or 34, wherein an inner coil is arranged to transmit energy to the outer element.

Embodiment 36 is a kit according to embodiment 35, wherein the inner coil is arranged to receive data from the outer element by wireless transmission.

Embodiment 37 is a kit according to any one of embodiments 33 to 36, wherein an outer coil is arranged to receive data from the inner element by wireless transmission.

Embodiment 38 is a kit according to any one of embodiments 33 to 37, wherein the inner element is the shaft of a percutaneous heart pump.

Embodiment 39 is a method of computing cardiac output (CO) of a living subject, wherein a mathematical model is constructed that links an input data vector with a target CO value.

Embodiment 40 is the method of embodiment 39, wherein said mathematical model is nonlinear.

Embodiment 41 is the method of embodiments 39 or 40, wherein said input data vector comprises at least one sensor measurement acquired by a medical invasive device according to any of the embodiments 1 to 32.

Embodiment 42 is the method of any one of embodiments 39 to 41, wherein said input data vector comprises physiologic input source data from said living subject.

Embodiment 43 is the method of any one of embodiments 39 to 42, wherein said input data vector comprises the area under the curve of a repeated temperature measurement.

Embodiment 44 is the method of any one of embodiments 39 to 43, wherein said input data vector comprises the area under the curve of a repeated temperature measurement after injection of a bolus of fluid into the venous circulation, whereby said injected bolus has a temperature different from the blood temperature.

Embodiment 45 is the method of any one of embodiments 39 to 44, wherein said input data vector comprises numbers derived from arterial pulse pressure analysis.

Embodiment 46 is the method of any one of embodiments 39 to 45, wherein said input data vector comprises numbers derived from arterial pulse pressure analysis, whereby said number is one of, beat-to-beat interval, beat rate, systolic pressure, diastolic pressure, pulse pressure, peak systolic pressure difference per time difference, area under the pulse curve and area under the systolic portion of a pulse pressure wave.

Embodiment 47 is the method of any one of embodiments 39 to 46, wherein said input data vector comprises at least one of: systolic pressure of said living subject, diastolic pressure of said living subject, and pulse pressure of said living subject.

Embodiment 48 is the method of any one of embodiments 39 to 47, wherein said input data vector comprises at least one of: age of said living subject, gender of said living subject, height of said living subject, weight of said living subject, and temperature of said living subject.

Embodiment 49 is the method of any one of embodiments 39 to 48, wherein said input data vector comprises at least one of: cardiac pump type, cardiac pump performance setting, cardiac pump size, cardiac pump blood flow, cardiac pump rotation speed, cardiac pump power consumption, cardiac pump electrical current consumption, cardiac pump pressure sensor reading.

Embodiment 50 is the method of any one of embodiments 39 to 49, wherein said target CO value is determined by an algorithm that comprises determining the area under the curve of a temperature measured repeatedly at multiple time points.

Embodiment 51 is the method of any one of embodiments 39 to 50, wherein the target CO value is determined by analysis of physiological signals measured by a medical invasive device according to any of the embodiments 1 to 32.

Embodiment 52 is the method of any one of embodiments 39 to 51, whereby generating the mathematical model comprises fitting said input data vector into said target CO value in a least-square optimal fashion.

Embodiment 53 is the method of any one of embodiments 39 to 52, whereby generating the mathematical model comprises training of an artificial neural network (ANN).

Embodiment 54 is the method of any one of embodiments 39 to 53, whereby generating the mathematical model comprises unsupervised training of a deep neural network (DNN).

Embodiment 55 is the method of any one of embodiments 39 to 53, whereby generating the mathematical model comprises supervised training of a deep neural network (DNN).

Embodiment 56 is the method of any one of embodiments 39 to 55, whereby generating the mathematical model comprises training of a deep believe network (DBN).

Embodiment 57 is the method of any one of embodiments 39 to 56, comprising: obtaining an input data vector; transforming said input data vector using at least said mathematical model; and expressing a result of said transformation as a CO value in physiologic units.

Embodiment 58 is the method of any one of embodiments 39 to 57, comprising: obtaining a plurality of said target CO values; generating said mathematical model based at least in part on said target CO values; obtaining an input data vector; transforming said input data vector using at least said mathematical model; and expressing a result of said transformation as a CO value in physiologic units.

Embodiment 59 is an apparatus comprising an arrangement to receive data transmitted by a medical invasive device according to any one of the embodiments 1 to 32.

Embodiment 60 is the apparatus of embodiment 59, wherein data are wirelessly transmitted by the medical invasive device.

Embodiment 61 is the apparatus of embodiment 59 or 60, comprising an arrangement to receive data, used for derivation of the input data vectors, transmitted from a second apparatus.

Embodiment 62 is the apparatus of embodiment 61, whereby the second apparatus is a medical monitor, defined as a device that is arranged to be placed in the same room as a patient and comprises a display arranged to display vital signs of said patient.

Embodiment 63 is the apparatus of embodiment 61 or 62, whereby the second apparatus is the control device of a heart pump.

Embodiment 64 is the apparatus of any one of embodiments 61 to 63, comprising an arrangement to receive data, used for derivation of the input data vectors, transmitted wirelessly from the second apparatus.

Embodiment 65 is the apparatus of any one of embodiments 60 to 64, whereby the wireless data transmission follows one of, the WiFi standard, the Bluetooth standard, the Ants standard.

Embodiment 66 is a computer program comprising a code structure arranged to implement a method according to any one of embodiments 39 to 58 when being executed on a computer.

Embodiment 67 is the apparatus according to any one of embodiments 59 to 65, comprising a computer program according to the embodiment 66.

Embodiment 68 is the apparatus according to any of embodiments 59 to 65 and to embodiment 67, comprising a display arranged to display at least cardio output (CO).

Embodiment 69 is the computer program according to embodiment 66, stored on a computer readable medium.

Embodiment 70 is a computer program product stored on a machine readable carrier, comprising program code means to implement a method according to any one of embodiments 39 to 58 when being executed on a computer.

The invention claimed is:

1. A medical invasive device that is an elongated sheath configured to receive and guide one of a shaft and a catheter, the medical invasive device comprising:
 a body portion that is arranged to be inserted into one of a patient's blood vessel, a patient's body cavity, and a patient's body tissue, wherein the body portion incorporates a sensor arrangement and a digital data transmission arrangement;
 an electronic circuit; and
 a harvesting unit that includes a receiving coil circuit, the harvesting unit arranged to harvest energy from an electromagnetic field, wherein the electromagnetic field is produced by a number of emitting coil circuits, and wherein an emitting coil circuit has a resonance frequency that is within one of 10% of the resonance frequency of the receiving coil circuit, 1% of the resonance frequency of the receiving coil circuit, and 0.1% of the resonance frequency of the receiving coil circuit.

2. The medical invasive device according to claim 1, wherein the body portion further incorporates an analog-to-digital conversion arrangement.

3. The medical invasive device according to claim 1, further comprising an outside portion that is arranged to be positioned outside a patient's body.

4. The medical invasive device according to claim 1, wherein the electronic circuit comprises a sensor arrangement including a temperature sensor, a pressure sensor, a vibration sensor, an ultrasound sensor, a light sensor, a voltage sensor, or one or more combinations thereof.

5. The medical invasive device according to claim 4, wherein the sensor arrangement comprises at least two sensors for measurement of different physical signals.

6. The medical invasive device according to claim 1, wherein the shaft received and guided is from one of a therapeutic device and a heart pump.

7. The medical invasive device according to claim 1, wherein the body portion has a transversal cross-sectional area of less than one of 60 square millimetres, 20 square millimetres, and 5 square millimetres.

8. The medical invasive device according to claim 1, wherein the electronic circuit comprises a wireless data transmission unit.

9. The medical invasive device according to claim 1, wherein the harvesting unit is arranged to harvest energy from energy sources that are not connected to the medical invasive device by wires.

10. The medical invasive device according to claim 9, wherein the harvesting unit comprises one of a vibration-based power generator and a thermoelectric generator.

11. A medical invasive device that is an elongated sheath configured to receive and guide one of a shaft and a catheter, the medical invasive device comprising:
  a body portion that is arranged to be inserted into one of a patient's blood vessel, a patient's body cavity, and a patient's body tissue, wherein the body portion incorporates a sensor arrangement and a digital data transmission arrangement;
  an electronic circuit; and
  a number of coil circuits arranged to harvest energy from an electromagnetic field in a frequency band selected from one of 5.725 GHz to 5.875 GHz, 2.4 GHz to 2.5 GHz, 902 MHz to 928 MHz, 13.553 MHz to 13.567 MHz, 6.765 MHz to 6.795 MHz, 235 kHz to 275 kHz, and 110 kHz to 205 kHz.

12. A kit comprising:
  an outer element that is a medical invasive device, the medical invasive device being an elongated sheath configured to receive and guide one of a shaft and a catheter, the medical invasive device comprising:
    a body portion that is arranged to be inserted into one of a patient's blood vessel, a patient's body cavity, and a patient's body tissue, wherein the body portion incorporates a sensor arrangement and a digital data transmission arrangement; and
    an electronic circuit;
  an inner element that is the shaft or the catheter that comprises a coil circuit, wherein the outer element covers at least a segment of the inner element, wherein an inner coil is arranged to transmit energy to the outer element.

13. The kit according to claim 12, wherein at least one of the inner coil is arranged to receive data from the outer element by wireless transmission, and an outer coil is arranged to receive data from an inner element by wireless transmission.

14. A kit comprising
  an outer element that is a medical invasive device, the medical invasive device being an elongated sheath configured to receive and guide one of a shaft and a catheter, the medical invasive device comprising:
    a body portion that is arranged to be inserted into one of a patient's blood vessel, a patient's body cavity, and a patient's body tissue, wherein the body portion incorporates a sensor arrangement and a digital data transmission arrangement; and
    an electronic circuit;
  an inner element that is the shaft of a percutaneous heart pump that comprises a coil circuit, wherein the outer element covers at least a segment of the inner element.

* * * * *